United States Patent [19]

Baldwin et al.

[11] 4,172,960
[45] Oct. 30, 1979

[54] PROCESS FOR PREPARING PYROGALLOL

[75] Inventors: Derek Baldwin; Peter S. Gates, both of Cambridge, England

[73] Assignee: Fisons Limited, London, England

[21] Appl. No.: 862,989

[22] Filed: Dec. 20, 1977

Related U.S. Application Data

[63] Continuation of Ser. No. 700,301, Jun. 28, 1976, abandoned.

[30] Foreign Application Priority Data

Jun. 28, 1975 [GB] United Kingdom ............... 27430/15
Jan. 24, 1976 [GB] United Kingdom ................. 2801/76

[51] Int. Cl.² ...................... C07C 39/08; C07C 43/22
[52] U.S. Cl. .................................... 568/772; 568/650
[58] Field of Search ............... 260/621 R, 625, 621 F, 260/613 D, 521, 473, 612 D; 568/772, 770, 763, 650

[56] References Cited

U.S. PATENT DOCUMENTS

| | | | |
|---|---|---|---|
| 2,100,228 | 11/1937 | Tinkler et al. | 260/621 F |
| 2,289,886 | 7/1942 | Scherling | 260/621 F |
| 2,697,732 | 12/1954 | Mavity | 260/621 F |
| 3,256,336 | 6/1966 | Lange | 260/621 F |
| 3,376,281 | 4/1968 | Cox | 260/613 D |
| 3,585,242 | 1/1971 | Roos et al. | 260/613 D |

OTHER PUBLICATIONS

English et al., "JACS", vol. 71 (1949), pp. 3310–3313.

*Primary Examiner*—Werren B. Lone
*Attorney, Agent, or Firm*—Wenderoth, Lind & Ponack

[57] ABSTRACT

Pyrogallol is prepared by (A) reacting a halo compound of formula

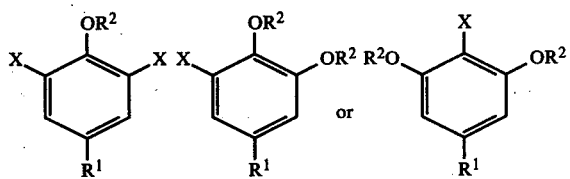

where X represents Br or I, R¹ represents hydrogen, secondary or tertiary alkyl of up to 10 carbon atoms, carboxy or alkoxycarbonyl of 2–5 carbon atoms and R² represents hydrogen or alkyl of 1–4 carbon atoms, with an alkali metal alkoxide of formula ROM where M represents an alkali metal and R represents alkyl of 1–4 carbon atoms, to replace each X by OR, and then (B) dealkylating each OR and each OR² where R² represents alkyl of 1–4 carbon atoms and removing the R¹ group where this is not hydrogen.

41 Claims, No Drawings

PROCESS FOR PREPARING PYROGALLOL

This invention relates to an improved process for preparing chemicals, in particular an improved process for preparing pyrogallol, 1,2,3-trihydroxybenzene:

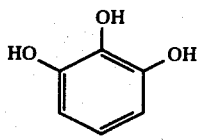

Pyrogallol has various uses, for instance as a photographic developer, in dyeing leather and wool, in the analysis of heavy metals and as an intermediate e.g. in the production of the insecticide 2,2-dimethyl-1,3-benzodioxol-4-yl methylcarbamate. At present, all the pyrogallol available in commerce is prepared by decarboxylation of gallic acid obtained from comparatively rare plant sources. This makes pyrogallol expensive and difficult to procure. We have now discovered a series of processes relating to the production of pyrogallol. They are advantageous particularly by reason of their convenience and high yields and purity of product. Especially advantageous are the processes provided for producing pyrogallol; these do not depend on such rare plant sources and they enable pyrogallol to be produced readily, in good yield and in a high state of purity.

Accordingly, the invention provides a process for preparing pyrogallol or a salt thereof, which process comprises (A) forming an ether of formula

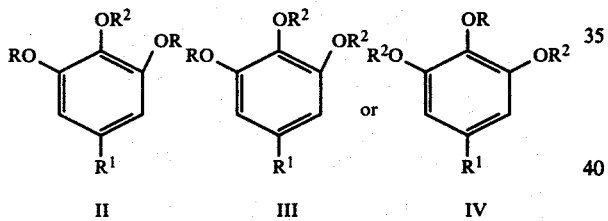

wherein
  R represents an alkyl group of 1–4 carbon atoms;
  $R^1$ represents a hydrogen atom, a secondary or tertiary alkyl group of up to 10 carbon atoms, carboxy or alkoxycarbonyl of 2–5 carbon atoms; and
  $R^2$ represents a hydrogen atom or an alkyl group of 1–4 carbon atoms;
  or a salt thereof
by a process comprising reacting the corresponding halo compound of formula

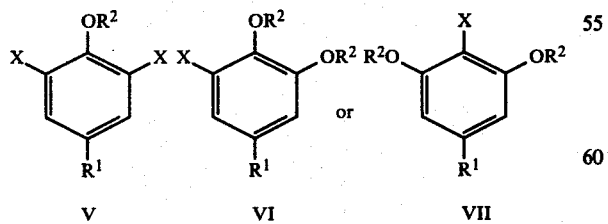

or a salt thereof, wherein $R^1$ and $R^2$ are as defined above and each X represents a bromine or iodine atom, with an alkali metal alkoxide of formula ROM where R is as defined above and M represents an alkali metal atom, and (B) reacting the ether of formula II, III or IV or salt thereof to dealkylate the OR group or groups and the $OR^2$ group or groups where $R^2$ represents an alkyl group of 1–4 carbon atoms and to remove the $R^1$ group where this is not hydrogen.

The invention also provides a process for preparing pyrogallol or a salt thereof, which process comprises dealkylating an ether of formula

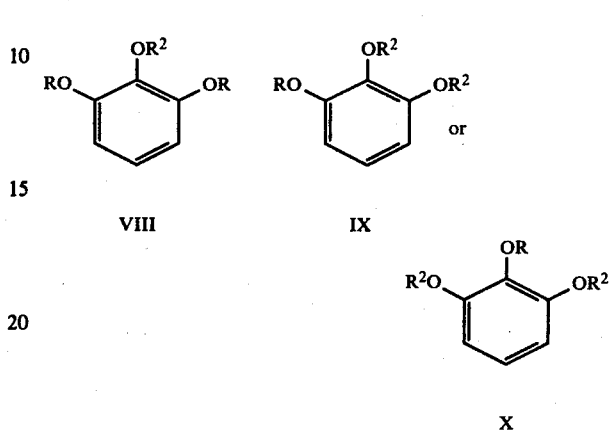

or a salt thereof, wherein R and $R^2$ are as defined above, by reacting it with aqueous hydrobromic acid.

The invention provides also a process for preparing pyrogallol or a salt thereof, which process comprises dealkylating a 5-alkylpyrogallol of formula

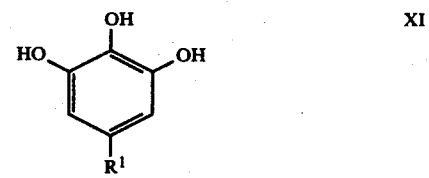

or a salt thereof, wherein $R^1$ represents a secondary or tertiary alkyl group of up to 10 carbon atoms, by reacting it with aqueous hydrobromic acid.

The invention also provides a process for preparing pyrogallol or a salt thereof, which process comprises reacting an alkylphenyl ether of formula

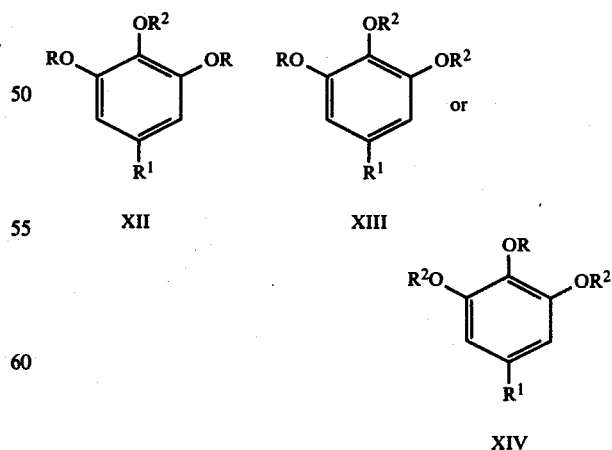

wherein $R^1$ represents a secondary or tertiary alkyl group of up to 10 carbon atoms and R and $R^2$ are as defined above, or a salt thereof, to dealkylate the OR group or groups and the $OR^2$ group or groups where $R^2$ represents an alkyl group of 1–4 carbon atoms and to remove the $R^1$ group.

In addition, the invention provides a process for preparing the ether of formula II, III or IV or a salt thereof, which process comprises reacting the corresponding halo compound of formula V, VI or VII or a salt thereof with an alkali metal alkoxide of formula ROM where R is as defined in formula II, III or IV and M represents an alkali metal atom.

The invention also provides a process for preparing the ether of formula VIII, IX or X, or a salt thereof, which process comprises removing the $R^1$ group of the corresponding ether of formula XII, XIII or XIV or a salt thereof.

The invention provides also a process for preparing the 5-alkylpyrogallol of formula XI or a salt thereof, which process comprises dealkylating the OR group or groups and the $OR^2$ group or groups where $R^2$ represents an alkyl group of 1–4 carbon atoms in an ether of formula XII, XIII or XIV.

The invention provides also a process for preparing the halo compound of formula V, VI or VII in which X represents a bromine atom, or a salt thereof, which process comprises reacting the corresponding compound of formula

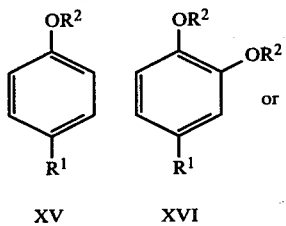

XV   XVI

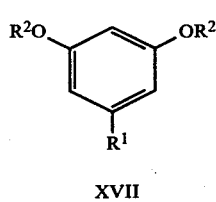

XVII or a salt thereof, where $R^1$ and $R^2$ are as defined above, with bromine in an aqueous medium.

Pyrogallol, the ether of formula II, III, IV, VIII, IX, X, XII, XIII or XIV, the 5-alkylpyrogallol of formula XI, the halo compound of formula V, VI or VII and the compound of formula XV, XVI or XVII may form salts. The pyrogallol, 5-alkylpyrogallol of formula XI, ether of formula II, III, IV, VIII, IX, X, XII, XIII or XIV, and halo compound of formula V, VI or VII produced by the present invention may be in the form of a salt, and a salt of the ether of formula II, III, IV, VIII, IX, X, XII, XIII or XIV, of the 5-alkylpyrogallol of formula XI, of the halo compound of formula V, VI or VII or of the compound of formula XV, XVI or XVII may be employed in the present invention. The salts can be prepared from the non-salt forms in ways known in themselves. Thus, where salts exist by reason of phenolic hydroxy groups being present, the salts include particularly alkali metal, e.g. sodium or potassium, especially sodium, salts, which can be prepared from the phenols themselves by reaction with alkali metal alkoxides or hydroxides. Where salts exist by reason of $R^1$ being carboxy, the salts include particularly alkali metal, e.g. sodium or potassium, especially sodium, salts, and the salts can be prepared from the acids themselves by reaction with alkalis e.g. sodium hydroxide. The non-salt forms can be prepared from the salts also in ways known in themselves, e.g. by reaction with acid for example hydrochloric acid.

Preferably the ether of formula II, III, IV, VIII, IX, X, XII, XIII or XIV, the 5-alkylpyrogallol of formula XI, the halo compound of formula V, VI or VII and the compound of formula XV, XVI or XVII rather than their salts are employed in the present processes. Normally a salt of the ether of formula II, III, IV, XII, XIII or XIV is first formed from the halo compound of formula V, VI or VII or salt thereof, and this ether salt is converted to the ether itself. Usually pyrogallol itself is first formed in the conversion of the ether of formula II, III, IV, VIII, IX, X, XII, XIII or XIV, the 5-alkylpyrogallol of formula XI or a salt of any of these, but the pyrogallol can be converted to its salts if desired though this is not preferred. The ether of formula VIII, IX or X rather than a salt thereof is usually first formed in the conversion from an ether of formula XII, XIII or XIV, or a salt thereof, but the ether of formula VIII, IX or X can be converted to its salts if desired though this is not preferred. The 5-alkylpyrogallol of formula XI rather than a salt thereof is usually first formed in the conversion from an ether of formula XII, XIII or XIV or salt thereof, but the 5-alkylpyrogallol can be converted to its salts if desired though this is not preferred. The halo compound of formula V, VI or VII rather than a salt thereof is usually first formed in the conversion from a compound of formula XV, XVI or XVII or salt thereof, but the halo compound can be converted to its salts if desired though this is not preferred.

In the present compounds, R preferably represents methyl, ethyl or n-propyl, e.g. methyl or ethyl, especially methyl. $R^1$ preferably represents hydrogen or a secondary or tertiary alkyl group of up to 8 carbon atoms (e.g. t-butyl, isopropyl or sec-amyl); hydrogen or a tertiary alkyl group is preferred, especially hydrogen or t-butyl. When $R^1$ represents an alkoxycarbonyl group, it is preferably a methoxycarbonyl or ethoxycarbonyl group. $R^2$ preferably represents hydrogen. Where there is more than one X, more than one R, or more than one $R^2$ group in the compounds involved in the present invention, the groups may be different but are conveniently the same.

The conversion of the ether of formula II, III or IV or salt thereof to pyrogallol or salt thereof involves (a) converting each alkoxy group on the benzene ring to hydroxy and (b) removing the $R^1$ group when this is not hydrogen. When $R^1$ represents a hydrogen atom only step (a) is involved. When $R^1$ represents other than hydrogen, the conversion can be carried out in 2 steps, corresponding to (a) and (b), conducted in either order.

Step (a) involves (i) dealkylating the ether of formula II, III or IV or salt thereof to the corresponding phenol of formula

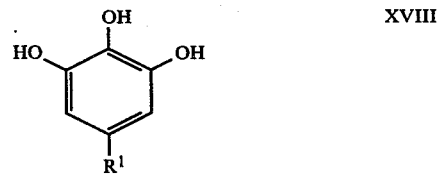

XVIII or a salt thereof, when (a) is carried out before (b), or (ii) dealkylating the ether of formula VIII, IX or X or salt thereof to pyrogallol or a salt thereof, when (b) is carried out before (a) or when $R^1$ represents a hydrogen atom.

Step (b) involves (i) removing the $R^1$ group when this is not hydrogen from the ether of formula II, III or IV or salt thereof, to give the corresponding ether of formula VIII, IX or X or salt thereof, when (b) is carried out before (a), or (ii) removing the $R^1$ group when this is not hydrogen from the phenol of formula XVIII or salt thereof, when (a) is carried out before (b).

Step (a) may be carried out for instance by reaction with acids especially aqueous hydrobromic acid, pyridine hydrochloride, pyridine hydrobromide, aluminum trichloride, boron tribromide, $BF_3.Et_2O$ in acetic anhydride, or an alkali metal (especially sodium) salt of ethyl mercaptan. Preferred is aqueous hydrobromic acid or pyridine hydrochloride. The step may be carried out for instance by heating e.g. at 50°–250° C. A separate solvent may be employed if desired.

When $R^1$ represents a secondary or tertiary alkyl group of up to 10 carbon atoms, step (b) may be carried out by heating e.g. at 50–350 preferably 150°–200° C., preferably in the presence of a dealkylation catalyst for example hydrogen chloride, hydrobromic acid, sulphuric acid, an alkyl sulphuric acid ester, tetraphosphoric acid, a sulphonic acid (e.g. p-toluenesulphonic acid), activated clay, a metal oxide (e.g. gamma alumina), aluminium chloride or a molecular compound of aluminum chloride with a phenol or alcohol. For example, the catalyst may be hydrogen chloride at high temperature e.g. 200–300 such as 250° C. and under pressure, attapulgous clay at 275°–350° C. or acid activated Fuller's earth at 250°–300° C. In a particular embodiment, the catalyst is a solid. Preferably however, step (b) is carried out using aqueous acids such as hydrobromic acid, e.g. at 50°–200° C. A separate solvent is not necessary. When $R^1$ represents carboxy, step (b) may be carried out in known ways or in ways known for related compounds; it may be carried out by heating e.g. at 50°–200° C., usually in the absence of solvent. When $R^1$ represents alkoxycarbonyl, step (b) may be carried out in known ways or in ways known for related compounds; it may be carried out by hydrolysing this $R^1$ group to carboxy, e.g. by acid or alkaline hydrolysis at 50°–150° C., and then proceeding as described for the case when $R^1$ represents carboxy.

Preferably, however, $R^1$ represents a secondary or tertiary alkyl group of up to 10 carbon atoms and steps (a) and (b) are carried out in a single stage. It is a particularly preferred and surprising feature of the present invention that this can be achieved. It is preferably achieved by reaction with aqueous hydrobromic acid.

The reaction with hydrobromic acid is usually carried out by heating, e.g. at a temperature of 50°–120° C., preferably by boiling under reflux. A separate solvent is not necessary.

The hydrobromic acid may be generated in situ by employing a weak base hydrobromide, though this is less convenient and more expensive and hence not preferred. Preferably 48% aqueous hydrobromic acid is employed.

In a preferred embodiment, pyrogallol is prepared by a process comprising reacting the alkylphenyl ether of formula XII, XIII or XIV with aqueous hydrobromic acid.

In another preferred embodiment, pyrogallol is prepared by a process comprising reacting the 5-alkylpyrogallol of formula XI or salt thereof with aqueous hydrobromic acid.

Pyrogallol and its salts absorb oxygen when hot and the salts absorb oxygen even at ambient temperature. Consequently, it may be desirable to produce the pyrogallol or salt thereof in an inert atmosphere, e.g. an atmosphere of nitrogen, carbon dioxide or hydrogen bromide, to avoid oxidation of the product.

The ether of formula II, III or IV or salt thereof can be prepared in a surprisingly advantageous way, by the reaction of the halo compound of formula V, VI or VII or salt thereof with the alkali metal alkoxide of formula ROM where R is as in formula II, III or IV and M represents an alkali metal atom. The alkali metal alkoxide can be obtained by dissolving the alkali metal in excess of the alcohol ROH, and the solution used directly in the present reaction. The reaction is usually carried out by heating, e.g. at a temperature of 50°–150° C. Suitably the reaction is conducted by heating in the presence of xylene and/or ROH as solvent, preferably by boiling under reflux. Additional solvent such as dimethylformamide can be employed. Desirably a catalyst is present, for example a transition metal catalyst especially a copper catalyst for example a cuprous salt such as cuprous chloride or cuprous bromide but preferably cuprous iodide. By a transition metal is meant an element of groups 1b, 2b, 3b, 4b, 5b, 6b, 7b and 8 of the Periodic Table as set out on page B3 of the 46th edition of the Handbook of Chemistry and Physics published by The Chemical Rubber Company.

The alkali metal alkoxide of formula ROM may be generated by co-distillation of alcohol ROH and water from a solution of alkali metal hydroxide in alcohol ROH with addition of alcohol ROH, e.g. when R represents methyl and M represents an atom of sodium.

The alkali metal M is usually sodium or potassium, preferably sodium. As stated above, when there is more than one X in the molecule, each X preferably represents the same halogen atom; this makes for easier production and reaction of the molecule. Preferably X represents a bromine atom.

Although the reaction of the halo compound of formula V, VI or VII, where X represents bromine or iodine, with the alkali metal alkoxide of formula ROM works well, yet surprisingly it does not work with the compound of formula V, VI or VII except that X represents chlorine, as is shown in the Examples.

The halo compound of formula V, VI or VII or a salt thereof can be prepared in known ways or in ways known for related compounds. Bromination can be effected in the absence of solvent or in the presence of a solvent e.g. carbon tetrachloride or toluene. Thus, 2,6-dibromophenol can be prepared by bromination of phenol in toluene in the presence of t-butylamine at −70° C. It has been found that the halo compound of formula V, VI or VII in which X represents a bromine atom, or a salt thereof, can surprisingly be prepared by a process comprising reacting the corresponding compound of formula XV, XVI or XVII, or a salt thereof, with bromine in an aqueous medium; preferably water is the sole solvent material. The aqueous hydrobromic acid obtained can be employed in a subsequent stage in the production of pyrogallol or a salt thereof. The reaction in an aqueous medium may be carried out for instance at a temperature of from −5 up to 120° C., preferably 15°–60° C.

Preferably, the ether of formula II, III or IV or salt thereof is of formula II or a salt thereof. Similarly, the ether of formula XII, XIII or XIV or salt thereof is preferably of formula XII or a salt thereof, the compound of formula XV, XVI or XVII or salt thereof is preferably of formula XV or a salt thereof, the ether of formula VIII, IX or X or salt thereof is preferably of formula VIII or a salt thereof, and the halo compound of formula V, VI or VII or salt thereof is preferably of formula V or a salt thereof.

Thus, in a preferred aspect, pyrogallol is prepared by a process comprising (A) forming 2,6-dimethoxyphenol or 2,6-dimethoxy-4-t-butylphenol by a process comprising reacting in the presence of a cuprous salt as catalyst 2,6-dibromophenol or a salt thereof, or 2,6-dibromo-4-t-butylphenol or a salt thereof, respectively with sodium methoxide, e.g. with a solution of sodium methoxide in methanol, and (B) dealkylating the 2,6-dimethoxyphenol or 2,6-dimethoxy-4-t-butylphenol, preferably by reaction with aqueous hydrobromic acid usually with heating.

In another preferred embodiment, pyrogallol is prepared by a process comprising dealkylating 2,6-dimethoxyphenol or 2,6-dimethoxy-4-t-butylphenol, preferably by reaction with aqueous hydrobromic acid. When 2,6-dimethoxy-4-t-butylphenol is employed, the reactants are preferably stirred vigorously.

In a further preferred embodiment, 2,6-dimethoxyphenol or a salt thereof, or 2,6-dimethoxy-4-t-butylphenol or a salt thereof, is prepared by a process comprising reacting 2,6-dibromophenol or a salt thereof, or 2,6-dibromo-4-t-butylphenol or a salt thereof, respectively in the presence of a cuprous salt as catalyst with sodium methoxide, preferably with a solution of sodium methoxide in xylene and/or methanol. The reaction is preferably conducted by admixing the bromo material and catalyst with a solution of the sodium methoxide, e.g. in xylene and/or methanol, and boiling under reflux. When methanol is used as the sole solvent, the methanolic solution is preferably concentrated (e.g. about 25% by weight sodium methoxide) to raise its boiling point to 90°–95° C.; this helps to reduce the time necessary for boiling under reflux. Preferably, however, xylene is used as solvent.

The present processes are conveniently conducted under ambient pressure.

The invention is illustrated by the following Examples, in which parts and percentages are by weight unless otherwise indicated.

EXAMPLE 1

A mixture of 2,6-dibromo-4-t-butylphenol (200 parts) and cuprous iodide (25 parts) in dimethylformamide (1,000 parts) was added to a solution of sodium (120 parts) in methanol (800 parts). The mixture was boiled under reflux for 3 hours and then cooled, filtered and poured into water (20,000 parts). Acidification with hydrochloric acid, extraction with ether and evaporating off the ether produced a red oil (123 parts) which was distilled to give 2,6-dimethoxy-4-t-butylphenol (105 parts, 77% yield), boiling point 89°–92° C./1 mm Hg.

EXAMPLE 2

The 2,6-dimethoxy-4-t-butylphenol produced in Example 1 was added to 48% aqueous hydrobromic acid (840 parts) and the mixture boiled under reflux with vigorous stirring in an atmosphere of nitrogen for 6 hours. The hydrobromic acid was then evaporated off under reduced pressure leaving a purple solid (52 parts, 83% yield) which was identified as crude pyrogallol. Purification with charcoal and recrystallisation from dichloroethane gave pure pyrogallol as a greyish-white solid, melting point 130°–132° C.

Analysis: Found: C, 57.07; H, 4.87%. $C_6H_6O_3$ requires: C, 57.14; H, 4.80%.

EXAMPLE 3

A mixture of 2,6-dibromophenol (prepared as described in Journal of Organic Chemistry, 1967, 32, 2358–2360) (145 parts) and cuprous iodide (20 parts) in dimethylformamide (1,000 parts) was added to a solution of sodium (103 parts) in methanol (800 parts). The mixture was boiled under reflux for 3 hours, then cooled, filtered and poured into cold water (20,000 parts). Acidification with hydrochloric acid, extraction with ether and evaporating off the ether produced an oil which solidified to give 2,6-dimethoxyphenol (54 parts, 60% yield), melting point 53°–56° C.

EXAMPLE 4

The product of Example 3 was added to 48% aqueous hydrobromic acid (400 parts) and the mixture boiled under reflux in an atmosphere of nitrogen for one hour. The hydrobromic acid was then evaporated off under reduced pressure to leave crude pyrogallol (40 parts, 90% yield), melting point 124°–130° C., the structure of which was confirmed by its nuclear magnetic resonance spectrum.

EXAMPLE 5

Sodium (7.1 g, 0.309 g atom) was dissolved in methanol (104 ml), 2,6-Dibromo-4-t-butylphenol (30 g), cuprous iodide (4 g, 0.021 mole) and xylene (168 ml) were added. Solvent (108 ml) was distilled from this mixture at atmospheric pressure to raise the reaction temperature to 85° C. The resulting mixture was boiled under reflux with stirring for 7 hours. Work up as given in Example 1 was followed using xylene as the extraction solvent. 2,6-Dimethoxy-4-t-butylphenol was obtained as a pale yellow oil, 20.1 g of 88% purity (90% yield).

EXAMPLE 6

Sodium (18.2 g, 0.79 g atom) was dissolved in methanol (152 ml). 2,6-Dibromo-4-t-butylphenol (30 g), cuprous bromide (4 g, 0.028 mole) and dimethylformamide (152 ml) were added and the mixture boiled under reflux (88°–84° C.) with stirring for 2 hours. Work up as given in Example 1 gave 2,6-dimethoxy-4-t-butylphenol as a pale yellow oil, 19.9 g of 90% purity (89% yield).

EXAMPLE 7

Sodium hydroxide (20 g) was dissolved in methanol (200 ml). Methanol was then distilled from the mixture under reduced pressure such that the boiling point of methanol was 40° C. with continuous addition of fresh methanol so as to maintain the volume at about 200 ml. This was continued until 5 l of methanol had been collected. A further 1 l was then distilled through the mixture at atmospheric pressure and the volume reduced to about 100 ml. 2,6-Dibromo-4-tert-butylphenol (15 g) and cuprous iodide (2 g) were then added and the mixture boiled under reflux for 18 hours. The mixture was then cooled, added to crushed ice and acidified with hydrochloric acid. Extraction with ether and evaporating off the ether gave 2,6-dimethoxy-4-tert-butylphenol (9.9 g), proved by its nuclear magnetic spectrum to be identical to the product obtained by the use of sodium methoxide in methanol and dimethylformamide.

EXAMPLE 8

2,6-Dibromo-4-t-butylphenol

Bromine (103 ml, 320 g, 2.0 mole) was added dropwise to a solution of p-t-butylphenol (150 g, 1.0 mole) in carbon tetrachloride (150 ml) at room temperature until the red colour persisted (monobromination). The solution was then heated to reflux and the rest of the bromine added portionwise over about 3 hours. Refluxing was continued for a further 20 hours prior to cooling, and washing with water, sodium bisulphite solution, sodium bicarbonate solution, and water again. The solution was then dried over sodium sulphate and run down leaving a pale yellow oil which crystallised. The yield was 308 g (100%), m.p. 65°-9° C. The product was pure enough (by NMR and GLC) for use without distillation.

EXAMPLES 9-20

2,6-Dimethoxy-4-t-butylphenol

Sodium (30 g, 1.3 g atom) was dissolved in methanol (250 ml). 2,6-Dibromo-4-t-butylphenol (49.3 g, 0.16 mole), cuprous iodide (6 g, 0.032 mole), and dimethylformamide (250 ml) were added and the mixture boiled under reflux with stirring for 3 hours. Addition to ice-water (2½ l) resulted in precipitation of the sodium salt of the title product. This aqueous suspension was acidified (hydrochloric acid) and shaken with ether. The aqueous solution was separated, and the ethereal layer filtered to remove the copper residue. The solid was washed with ether, the aqueous phase extracted twice more and all the extracts combined. After washing with sodium thiosulphate solution (to remove a trace of iodine) and water, drying over sodium sulphate and running down, the title product was obtained as a pale yellow oil, 32.2 g (96% yield). NMR showed total replacement of bromine and the product was 98.4% pure by GLC. Distillation of a portion gave a fraction boiling at 89°-92° C./0.1 mm with an identical NMR spectrum to the crude product.

In further Examples, these conditions and reagents were varied as set out in the following table, in which DMF stands for dimethylformamide:

| Example | Base | Catalyst | Solvent(s) | Conditions | % replacement of Br (by NMR) |
|---|---|---|---|---|---|
| 10 | NaOH | CuI | n-PrOH | Distillation/Addition of solvent 3 hours Reflux 2 hours | 20% |
| 11 | NaOme | CuI | MeOH | Reflux 5 hours | 100% |
| 12 | NaOH | CuI | MeOH/BMF | Distillation/Addition of MeOH 3 hours Reflux 3 hours | 90% |
| 13 | NaOMe | CuBr | MeOH | Reflux 5 hours | >90% |
| 14 | NaOMe | CuCl | MeOH | Reflux 5 hours | >90% |
| 15 | NaOH | CuI | MeOH | Distillation/Addition of MeOH 2 hours Reflux 6 hours | 25% |
| 16 | NaOH | CuI | MeOH | Distillation/Addition during course of reaction 20 hours | 50% |
| 17 | NaOH | CuI | MeOH | Distillation/Addition of MeOH 10 hours Reflux 6 hours | 75% |
| 18 | MaOH | CuI | MeOH | Very fast distillation/addition of MeOH 4 hours Reflux 6 hours | 60% |
| 19 | NaOH | CuI | MeOH | Fast distillation/addition under partial vacuum 6 hours Reflux 18 hours | 100% |
| 20 | NaOH | CuI | MeOH | Reflux 24 hours through 3A molecular sieve in soxhlet extractor | 30% |

EXAMPLE 21

2,6-Dimethoxyphenol 2,6-Dibromophenol (14.5 g, 0.058 mole) was treated with sodium methoxide (from 10.3 g sodium, 0.45 g atom) in methanol (100 ml) and dimethylformamide (100 ml) in the presence of cuprous iodide (2 g) in the same way as described in detail for 2,6-dibromo-4-t-butylphenol in Example 9. The crude yield of title product was 5.4 g (60%), m.p. 53°-6° C. (literature gives 55°-6° C.). The lower yield may be explained by incomplete extraction, 2,6-dimethoxyphenol being to some extent water soluble.

EXAMPLES 22–26

Attempts to prepare 2,6-dimethoxyphenol from 2,6-dichlorophenol

EXAMPLE 22

NaOMe/CuI/MeOH, reflux 48 hours (93° C.)—unchanged, very small trace—OMe in NMR spectrum.

EXAMPLE 23

NaOMe/CuI/Dimethyl sulphoxide, reflux 1½ hours (164° C.)—unchanged (NMR).

EXAMPLE 24

NaOMe/CuI/Quinoline, reflux 3 hours (230° C.)—very impure starting material, possible contaminant o-chlorophenol—no methoxy (NMR).

EXAMPLE 25

NoOMe/CuI/collidine, reflux 20 hours (170° C.)—As Example 24.

EXAMPLE 26

NaOMe/AgOAc/MeOH/DMF, reflux 6 hours—unchanged (NMR).

EXAMPLE 27

NaOH/H$_2$O/Cu$_2$O, reflux 7 hours—80% recovered starter, 20% solid m.p 260° C. (? polymer).

EXAMPLE 28

Attempt to prepare 2,6-dimethoxy-4-t-butylphenol from 2,6-dichloro-4-t-butylphenol Sodium (24.3 g, 1.06 g atom) was dissolved in methanol (57.3 mls). 2,6-Dichloro-4-t-butylphenol (28.2 g, 0.128 mole), cuprous iodide (4.4 g, 0.025 mole) and dimethylformamide (180 mls) were added and the mixture boiled under reflux (90° C.) with stirring for 6 hours. The product (26.8 g) isolated as in Example 1 contained no 2,6-dimethoxy-4-t-butylphenol.

EXAMPLE 29

3,5-Dimethoxy-4-hydroxybenzoic acid (syringic acid)

3,5-Dibromo-4-hydroxybenzoic acid (60 g) was treated with sodium methoxide in methanol (prepared by dissolving 32 g sodium in 300 ml methanol), cuprous iodide (7.5 g) and dimethylformamide (300 ml) under the same conditions as described for 2,6-dibromo-4-t-butylphenol in Example 9. 34.5 g (theory 39.5 g) of a solid m.p. 210°–6° C. (literature: 204°–5° C. for the dimethoxy compound) was isolated and this was proved by NMR to be 80% 3-bromo-4-hydroxy-5-methoxybenzoic acid, 10% title product and 10% starting material (50% total replacement of Br).

EXAMPLE 30

4-Bromo-3,5-dihydroxybenzoic acid

α-Resorcylic acid (100 g, 0.65 mole) was brominated in acetic acid (300 ml) (104 g, 0.65 mole bromine) yielding 139 g title product (92%) m.p. 260°–3° C. (literature: 253° C.).

EXAMPLE 31

4-Methoxy-3,5-dihydroxybenzoic acid

Treatment of 4-bromo-3,5-dihydroxybenzoic acid (23.3 g, 0.1 mole) with sodium methoxide (18.5 g, 0.8 g atom) in an analogous procedure to that of Example 9 with a 9 hour reflux yielded 12 g (theory 18.4 g) of a white solid, m.p 238°–42° C. NMR showed this to be 45% title product and 55% starting material.

EXAMPLES 32–35

Pyrogallol

EXAMPLE 32

2,6-Dimethoxy-4-t-butylphenol (15 g, 0.072 mole) was added to 48% aqueous hydrobromic acid (120 ml) and the mixture boiled under reflux in a nitrogen atmosphere with vigorous stirring for 1 hour (until a single phase resulted). Water (120 ml) was added and refluxing was continued for a further 20 hours. Running down gave 10.8 g solid which was found by NMR to be 80% 5-t-butylpyrogallol and 20% pyrogallol. A further 200 ml 48% hydrobromic acid was added and the mixture refluxed as before for 6 hours. Running down gave a dark mauve solid m.p. 121°–6° C. which was shown by NMR to be pyrogallol. The yield was 7.7 g (86%).

EXAMPLE 33

Example 32 was repeated with 38 g 2,6-dimethoxy-4-t-butylphenol and 250 ml 48% aqueous hydrobromic acid with omission of the water addition, refluxing with vigorous stirring being carried out for 7 hours. Running down gave 19.6 g (86%) crude pyrogallol, m.p. 119°–25° C. Comparison with Example 32 shows that omission of the water addition is advantageous. Recrystallisation of a 17 g sample of the crude pyrogallol from 1,2-dichloroethane with charcoaling gave 12 g pale pink solid (70% recovery), pure pyrogallol, m.p. 130°–2°.

Found: C 57.07, H 4.87. C$_6$H$_6$O$_3$ requires: C 57.14, H 4.80%.

EXAMPLE 34

In a similar Example to that of Example 33 but without stirring and on a smaller scale (5 g) debutylation was almost complete in 2 hours (4% t-butylpyrogallol left).

EXAMPLE 35

2,6-Dimethoxyphenol (5.4 g, 0.035 mole) and 48% aqueous hydrobromic acid (40 ml) were boiled under reflux in a nitrogen atmosphere for 1 hour. Running down gave 4 g (91%) magenta-coloured solid m.p. 124°–30° C. which was identified by NMR as pyrogallol.

EXAMPLE 36

5-t-Butylpyrogallol 2,6-Dimethoxy-4-t-butylphenol (16.5 g, 0.08 mole) and pyridine hydrochloride (60 g) were heated at 200°–210° C. for 2 hours. The mixture was then added to iced dilute hydrochloric acid and the aqueous solution extracted twice with petroleum ether (b.p. 40°–60° C.) to remove any unchanged starter. The aqueous phase was saturated with salt and extracted three times with ether. Drying and running down gave 12.5 g title product (88%) m.p. 137°–9° C.

EXAMPLE 37

Pyrogallol from 2,6-dimethoxy-4-t-butylphenol 2,6-Dimethoxy-4-t-butylphenol (81 g, 0.38 mole) and HBr solution were refluxed under a nitrogen blanket with vigorous stirring for 12 hours at about 120° C. in a 1 liter baffled flask fitted with mechanical stirrer, condenser, thermometer and nitrogen inlet. After 2–3 hours the initial 2 phases (oil/aqueous) became one and the solution turned back. The excess of HBr solution was then distilled off (nitrogen blanket) at 20 mm pressure (pot temperature 60° C.), leaving 63.7 g of a viscous black oil of 67% pyrogallol content. This was given 5 minute extractions with 4×200 ml portions of boiling dichloroethane. The decanted dichloroethane extracts were combined, boiled with 2 g Norit Ultra charcoal and filtered. The filtrate was distilled (nitrogen blanket) to dryness at 20 mm pressure. The resulting white solid was dried in an air oven at 60° C. The product was identified as pyrogallol; yield 43.2 g (89% theory), 98.3% pure, mp 130°-132° C.

EXAMPLE 38

Preparation of 2,6-dibromo-4-t-butylphenol

To 150 g (1.0 mole) 4-t-butylphenol in 150 mls water in a flask fitted with mechanical stirrer, condenser and HBr water trap, thermometer and bromine reservoir, was added in 1 hour 320 g (2.0 moles) bromine, starting at room temperature and allowing the temperature to rise to 56° C.

After the addition, the crystalline slurry was cooled to 15° C., filtered and the product washed with 450 mls water. The white crystalline product was dried in an oven at 40° C. to give 302.5 g of 97% pure material m.p. 69°-71° C. (97% yield).

We claim:

1. A process for preparing pyrogallol or a salt thereof, which process comprises
(A) forming an ether of formula

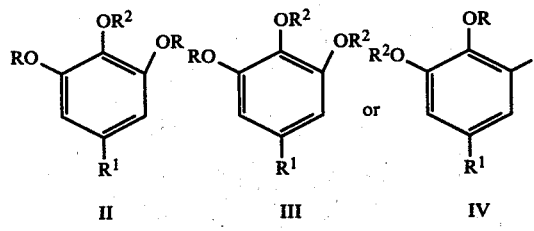

or a salt thereof, wherein R represents an alkyl group of 1-4 carbon atoms; $R^1$ represents a hydrogen atom, a secondary or tertiary alkyl group of up to 10 carbon atoms, carboxy or alkoxycarbonyl of 2-5 carbon atoms; and $R^2$ represents a hydrogen atom or an alkyl group of 1-4 carbon atoms; by a process comprising heating at a temperature of 50° to 150° C. the corresponding halo compound of formula

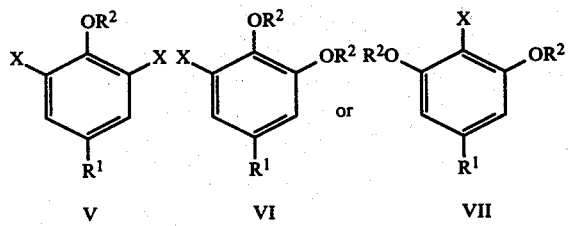

or a salt thereof, wherein $R^1$ and $R^2$ are as defined above and each X represents a bromine or iodine atom, with an alkali metal alkoxide of formula ROM where R is as defined above and M represents an alkali metal atom, and
(B) reacting the ether of formula II, III or IV or salt thereof to dealkylate the OR group or groups and the $OR^2$ group or groups where $R^2$ represents an alkyl group of 1-4 carbon atoms and to remove the $R^1$ group where this is not hydrogen by a process comprising heating with an acid selected from the group consisting of aqueous hydrobromic acid, pyridine hydrochloride, pyridine hydrobromide, aluminum trichloride, boron tribromide, $BF_3 \cdot Et_2O$ in acetic anhydride, and an alkali metal salt of ethyl mercaptan at a temperature of 50° to 250° C.

2. A process according to claim 1 wherein the ether is of formula II and the halo compound is of formula V.

3. A process according to claim 1 wherein the reaction with an alkali metal alkoxide is conducted in the presence of a cuprous salt as catalyst.

4. A process according to claim 1 wherein $R^2$ represents a hydrogen atom.

5. A process according to claim 1 wherein R represents a methyl group.

6. A process according to claim 1 wherein M represents a sodium atom.

7. A process according to claim 1 wherein X represents a bromine atom.

8. A process according to claim 1 wherein $R^1$ represents a hydrogen atom.

9. A process according to claim 1 wherein $R^1$ represents a secondary or tertiary alkyl group of up to 10 carbon atoms.

10. A process according to claim 9 wherein $R^1$ represents t-butyl.

11. A process according to claim 9 wherein the dealkylation of the OR group or groups and the $OR^2$ group or groups where $R^2$ represents an alkyl group of 1-4 carbon atoms and the removal of the $R^1$ group are carried out in a single stage.

12. A process according to claim 1 wherein $R^1$ represents a hydrogen atom or a secondary or tertiary alkyl group of up to 10 carbon atoms, and the dealkylation of the OR group or groups and the $OR^2$ group or groups where $R^2$ represents an alkyl group of 1-4 carbon atoms and the removal of the $R^1$ group where this is not hydrogen are carried out by heating with aqueous hydrobromic acid at a temperature of 50° to 250° C.

13. A process for preparing pyrogallol, which process comprises
(A) forming 2,6-dimethoxyphenol by a process comprising heating at a temperature of 50° to 150° C. 2,6-dibromophenol or a salt thereof with sodium methoside in the presence of a cuprous salt as catalyst, and
(B) dealkylating the 2,6-dimethoxyphenol by a process which comprises heating it with an acid selected from the group consisting of aqueous hydrobromic acid, pyridine hydrochloride, pyridine hydrobromide, aluminum trichloride, boron tribromide, $BF_3 \cdot Et_2O$ in acetic anhydride, and an alkali metal salt of ethyl mercaptan at a temperature of 50° to 250° C.

14. A process for preparing pyrogallol, which process comprises
(A) forming 2,6-dimethoxy-4-t-butylphenol by a process comprising heating at a temperature of 50° to 150° C. 2,6-dibromo-4-t-butylphenol or a salt thereof with sodium methoxide in the presence of a cuprous salt as catalyst, and
(B) dealkylating the 2,6-dimethoxy-4-t-butylphenol by a process which comprises heating with an acid selected from the group consisting of aqueous hydrobromic acid, pyridine hydrochloride, pyridine hydrobromide, aluminum trichloride, boron tribromide, BF$_3$·Et$_2$O in acetic anhydride, and an alkali metal salt of ethyl mercaptan at a temperature of 50° to 250° C.

15. A process according to claim 13 wherein stage (B) is effected by heating the 2,6-dimethoxyphenol with aqueous hydrobromic acid at a temperature of 50° to 250° C.

16. A process according to claim 14 wherein stage (B) is effected by heating the 2,6-dimethoxy-4-t-butylphenol with aqueous hydrobromic acid at a temperature of 50° to 250° C.

17. A process for preparing an ether of formula II, III or IV as defined in claim 1, or a salt thereof, which process comprises heating at a temperature of 50° to 150° C. the corresponding halo compound of formula V, VI or VII as defined in claim 1, or a salt thereof, with an alkali metal alkoxide of formula ROM wherein R is an alkyl group of 1 to 4 carbon atoms and M is an alkali metal atom.

18. A process according to claim 17 wherein the ether is of formula II and the halo compound is of formula V.

19. A process according to claim 17 wherein the reaction is conducted in the presence of a cuprous salt as catalyst.

20. A process according to claim 17 wherein R$^2$ represents a hydrogen atom.

21. A process according to claim 17 wherein R represents a methyl group.

22. A process according to claim 17 wherein M represents a sodium atom.

23. A process according to claim 17 wherein X represents a bromine atom.

24. A process according to claim 17 wherein R$^1$ represents a hydrogen atom.

25. A process according to claim 17 wherein R$^1$ represents a secondary or tertiary alkyl group of up to 10 carbon atoms.

26. A process according to claim 25 wherein R$^1$ represents t-butyl.

27. A process according to claim 17, wherein 2,6-dimethoxyphenol or a salt thereof is prepared by a process comprising heating at a temperature of 50° to 150° C. 2,6-dibromophenol or a salt thereof with sodium methoxide in the presence of a cuprous salt as catalyst.

28. A process according to claim 17, wherein 2,6-dimethoxy-4-t-butylphenol or a salt thereof is prepared by a process comprising heating at a temperature of 50° to 150° C. 2,6-dibromo-4-t-butylphenol or a salt thereof with sodium methoxide in the presence of a cuprous salt as catalyst.

29. A process for preparing pyrogallol or a salt thereof, which process comprises reacting an alkylphenyl ether of formula

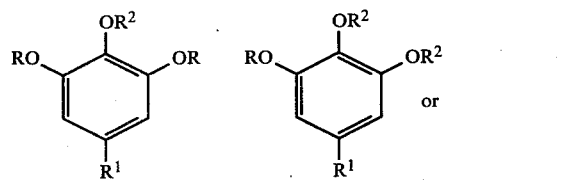

XII  XIII

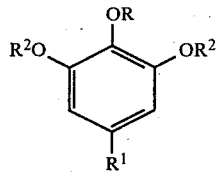

XIV or a salt thereof, wherein R$^1$ represents a secondary or tertiary alkyl group of up to 10 carbon atoms and R and R$^2$ are as defined in claim 1, or a salt thereof, to dealkylate the OR group or groups and the OR$^2$ group or groups where R$^2$ represents an alkyl group of 1–4 carbon atoms and to remove the R$^1$ group, by a process comprising heating with an acid selected from the group consisting of aqueous hydrobromic acid, pyridine hydrochloride, pyridine hydrobromide, aluminum trichloride, boron tribromide, BF$_3$·Et$_2$O in acetic anhydride, and an alkali metal salt of ethyl mercaptan at a temperature of 50° to 250° C.

30. A process according to claim 29 wherein the dealkylation and the removal of the R$^1$ group are carried out in a single stage.

31. A process according to claim 30 wherein the ether or salt thereof is heated with aqueous hydrobromic acid at a temperature of 50° to 250° C.

32. A process according to claim 29 wherein R$^2$ represents a hydrogen atom.

33. A process according to claim 29 wherein R represents a methyl group.

34. A process according to claim 29 wherein R$^1$ represents t-butyl.

35. A process for preparing pyrogallol or a salt thereof, which process comprises dealkylating a 5-alkylpyrogallol of formula

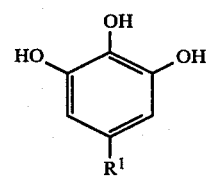

XI or a salt thereof, wherein R$^1$ represents a secondary or tertiary alkyl group of up to 10 carbon atoms, by heating it with aqueous hydrobromic acid at a temperature of 50° to 250° C.

36. A process for preparing pyrogallol or a salt thereof, which process comprises dealkylating an ether of formula

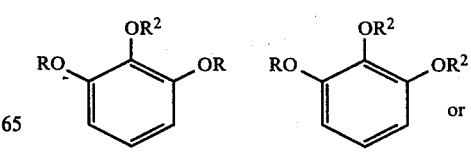

VIII  IX or a salt thereof, wherein R and R² are as defined in claim 1, by heating it with aqueous hydrobromic acid at a temperature of 50° to 250° C.

37. A process according to claim 36 wherein R² represents a hydrogen atom.

38. A process according to claim 36 wherein R represents a methyl group.

39. A process according to claim 35 wherein R¹ represents t-butyl.

40. A process for preparing the ether of formula VIII, IX or X as defined in claim 36, or a salt thereof, which process comprises removing the R¹ group of the corresponding ether of formula XII, XIII or XIV wherein R represents an alkyl group of 1–4 carbon atoms, R¹ represents a secondary or tertiary alkyl group of up to 10 carbon atoms and R² represents a hydrogen atom or an alkyl group of 1–4 carbon atoms or a salt thereof by a process which comprises heating the ether at a temperature of 50° to 350° C.

41. A process for preparing the 5-alkyl-pyrogallol of formula XI as defined in claim 35, or a salt thereof, which process comprises dealkylating the OR group or groups and the OR² group or groups where R² represents an alkyl group of 1–4 carbon atoms in an ether of formula XII, XIII, or XIV wherein R represents an alkyl group of 1–4 carbon atoms, R¹ represents a secondary or tertiary alkyl group of up to 10 carbon atoms and R² represents a hydrogen atom or an alkyl group of 1–4 carbon atoms or a salt thereof by a process which comprises heating the ether with an acid selected from the group consisting of aqueous hydrobromic acid, pyridine hydrochloride, pyridine hydrobromide, aluminum trichloride, boron tribromide, BF₃·Et₂O in acetic anhydride, and an alkali metal salt of ethyl mercaptan at a temperature of 50° to 250° C.

* * * * *